July 18, 1939. W. I. JOHNSTON Plant Pat. 335
ROSE PLANT
Filed Dec. 17, 1938
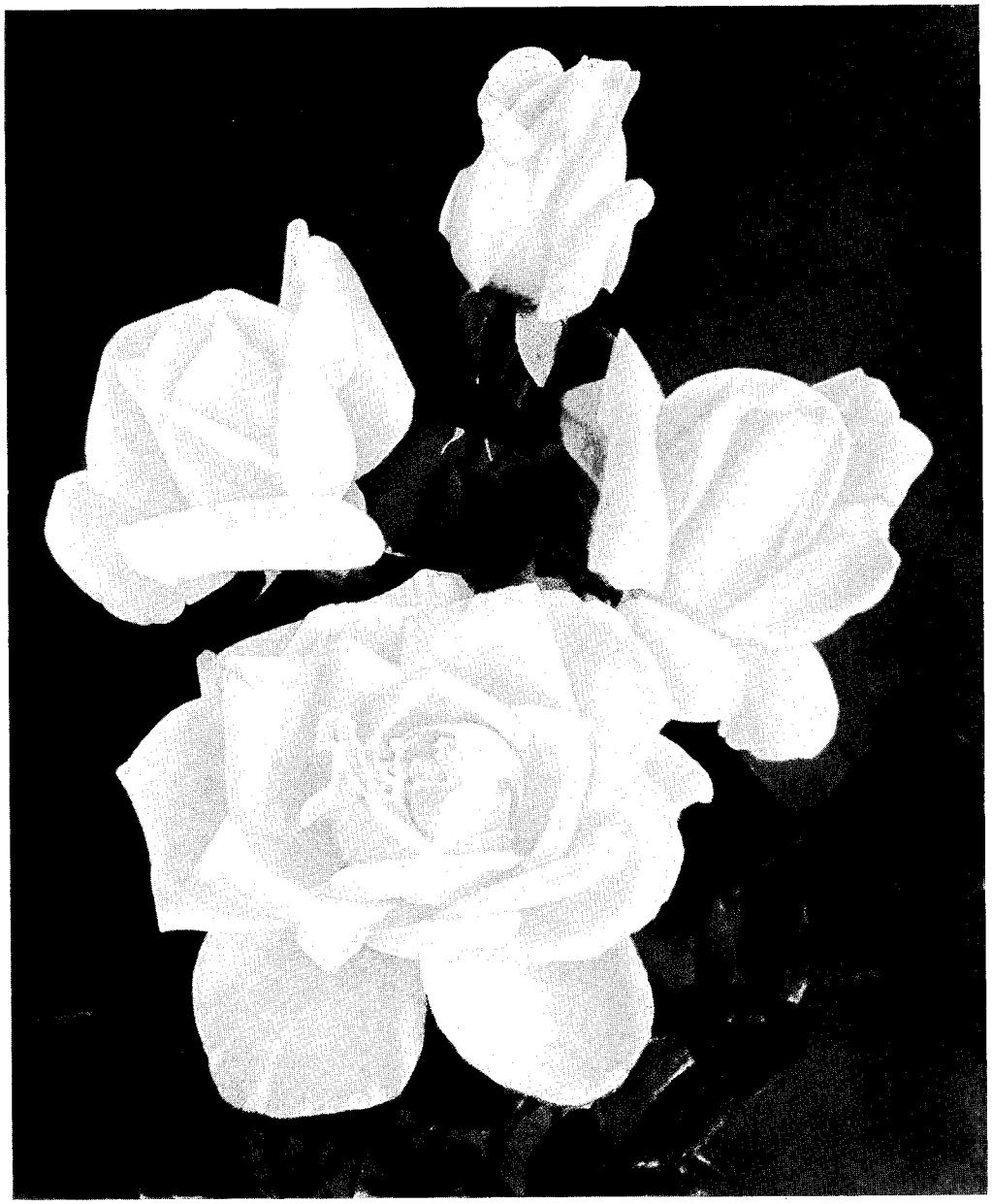
Inventor
Walter Irwin Johnston
By Robb & Robb
Attorneys Patented July 18, 1939

UNITED STATES PATENT OFFICE

335

ROSE PLANT

Walter Irwin Johnston, Portadown, Ireland, assignor to Jackson & Perkins Company, Newark, N. Y.

Application December 17, 1938, Serial No. 246,468

1 Claim. (Cl. 47—61)

This invention relates to a new and distinct variety of Hybrid Tea rose plant.

The object in view in the origination of this rose was to obtain a superior rose for garden and exhibition purposes. In its accomplishment, this objective was achieved to a marked degree for in form and size of the flower it makes an ideal exhibition rose.

A further and dominating distinction is found in the color of the flower which is different from any other similar rose of which I am aware. This distinction is found in the fact that the clarity of the white appearance of the flower is softened at its base by a Martius Yellow glow.

The possession of the foregoing novel characteristics combined with the vigorous habit of growth of the bush and the abundance of the exhibition flowers makes this variety an ideal rose for display, for garden use, and for cutting purposes.

The new variety has been asexually reproduced and its novel characteristics have been found to come true to form.

The following is a detailed description of the new variety, all color terminology being in accord with Ridgway's Color Standard:—

Parentage:

*Seed parent.*—Florence L. Izzard.

*Pollen parent.*—Mrs. Charles Lamplough.

Classification:

*Botanic and commercial.*—Hybrid Tea.

*Flower*

(Observations made in fields and gardens of Jackson & Perkins Company, Newark, New York, in the morning of June 26, 1938.)

Blooming habit:

Recurrent—continuous.

Bud:

*Size.*—Very large.

*Form.*—Pointed; is not affected by hot weather, but is affected by wet weather since it balls some.

*Color.*—When sepals first divide — White. When petals begin to unfurl—Plate 5, Sulphur Yellow. When half blown: inside of petals—White; reverse of petals—Plate 5, Sulphur Yellow.

*Sepals.*—Serrated, branched; curl back when bud half open.

*Calyx.*—Shape—funnel; size—broad; aspect—smooth.

*Peduncle.*—Length — long; aspect — smooth; color—under, Plate 31, Light Cress Green; upper, Plate 27, Corinthian Red. Strength—stiff, erect; heavy.

*Opening.*—Bud opens well; is sometimes affected by adverse conditions.

Bloom:

*Size.*—Very large.

*Average size when fully expanded.*—Five inches.

*Borne.*—Several together.

*Stems.*—Long; strong.

*Form.*—When first open—high center; permanence—retains its form to the end.

*Petalage.*—Double (full but open center); number of petals under normal conditions—30.

*Color.*—Center of flower—White with Plate 4 Martius Yellow; outer petals—White; base of petals (aiglet)—Plate 4, Lemon Chrome; inside of petals—White; reverse of petals—White; base—Plate 4, Martius Yellow.

Petals:

*Texture.*—Thick; is not affected by wet or hot weather.

*Appearance.*—Inside—satiny; outside—satiny.

*Form.*—Oval.

*Arrangement.*—Informal (with "rags" in center); petaloids in center—few.

*Persistence.*—Drop off cleanly.

*Fragrance.*—Slight; nature—Sweet Briar.

*Lasting quality.*—On the plant and as cut flowers, fair.

Genital organs:

*Stamens, anthers.* — Size — medium; many. Color — Primuline Yellow. Arrangement — regular round styles, tucked in calyx or partly so, mixed with petaloids.

*Stamens, filaments (threads).*—Long. Color—Plate 16, Wax Yellow.

*Pollen.*—Plate 16, Mustard Yellow.

*Styles.*—Uneven length; size—medium.

*Stigmas.*—Plate 16, Straw Yellow.

*Ovaries.*—All enclosed in calyx.

Fruit:

Variety is fertile with its own pollen.

*Form.*—Ovoid.

*Aspect.*—Smooth.

*Sepals.*—Permanent; recurved.

*Plant*

Form:

Bush.

Growth:

Vigorous, upright, branching.

Foliage:

5 to 7 leaflets.

*Size.*—Large.
*Quantity.*—Normal.
*Color.*—New foliage: upper side—Plate 16, Roman Green; edge—Plate 13, Hessian Brown; under side—Plate 14, Liver Brown. Old foliage: upper side—Plate 31, Dark Cress Green; under side—Plate 31, Light Cress Green.
*Shape.*—Oval pointed.
*Texture.*—Upper side—leathery, flat; under side—smooth. Ribs and veins—ordinary.
*Edge.*—Serrated (saw toothed).
*Serration.*—Single; small.
*Rachis.*—Color—Plate 31, Cress Green. Under side—prickles.
*Stipules.*—Short, serrated.
*Disease resistance.*—Susceptible to black spot.

Wood:
*New wood.*—Color—Plate 14, Liver Brown. Bark—Smooth.
*Old wood.*—Color—Plate 31, Light Cress Green. Bark—smooth.

Thorns (divided into thorns, prickles and short needles):
*Thorns.*—Quantity: on main stalks from base—ordinary; on laterals from stalk—ordinary. Form—broad base, medium length, hooked downward. Color when young—Plate 38, Neutral Red. Position—irregular.
*Prickles.*—Quantity: on main stalks—few; on laterals—few. Color—Plate 38, Neutral Red.

I claim:

A new and distinct variety of Hybrid Tea rose plant, characterized as to novelty by its vigorous habit of growth and the abundance of white exhibition flowers softened by a Martius Yellow glow at their bases, substantially as shown and described.

WALTER IRWIN JOHNSTON.